(12) United States Patent
Kumar et al.

(10) Patent No.: US 6,900,264 B2
(45) Date of Patent: May 31, 2005

(54) COMPOSITIONS COMPRISING RIGID-ROD POLYMERS AND CARBON NANOTUBES AND PROCESS FOR MAKING THE SAME

(75) Inventors: Satish Kumar, Lawrenceville, GA (US); Fred E. Arnold, Centerville, OH (US); Thuy D. Dang, Centerville, OH (US)

(73) Assignee: Georgia Tech Research Corporation, Atlanta, GA (US)

( * ) Notice: Subject to any disclaimer, the term of this patent is extended or adjusted under 35 U.S.C. 154(b) by 288 days.

(21) Appl. No.: 10/228,483

(22) Filed: Aug. 27, 2002

(65) Prior Publication Data

US 2003/0083421 A1 May 1, 2003

Related U.S. Application Data

(60) Provisional application No. 60/315,583, filed on Aug. 29, 2001.

(51) Int. Cl.[7] .................................................. C08K 3/34
(52) U.S. Cl. ...................... 524/495; 524/496
(58) Field of Search ................. 524/495, 496

(56) References Cited

U.S. PATENT DOCUMENTS

| | | | |
|---|---|---|---|
| 3,632,414 A | 1/1972 | Arnold et al. | 117/124 |
| 3,901,855 A | 8/1975 | Arnold | 260/78.4 |
| 4,533,693 A | 8/1985 | Wolfe et al. | 524/417 |
| 5,001,217 A | 3/1991 | Tsai et al. | 528/337 |
| 5,039,778 A | 8/1991 | Dang et al. | 528/183 |
| 5,041,522 A | 8/1991 | Dang et al. | 528/183 |
| 5,098,988 A | 3/1992 | Tsai et al. | 528/183 |
| 5,136,012 A | 8/1992 | Dang et al. | 528/183 |
| 5,276,085 A | 1/1994 | Kasowski et al. | 524/606 |
| 5,312,876 A | 5/1994 | Dang et al. | 525/435 |
| 5,312,895 A | 5/1994 | Dang et al. | 528/337 |
| 5,512,368 A * | 4/1996 | Harmer et al. | 428/364 |
| 5,674,967 A | 10/1997 | Goodwin | 528/42 |
| 5,997,832 A | 12/1999 | Lieber et al. | 423/249 |
| 6,203,814 B1 | 3/2001 | Fisher et al. | 424/443 |
| 6,680,016 B2 * | 1/2004 | Wang et al. | 264/105 |

FOREIGN PATENT DOCUMENTS

| | | |
|---|---|---|
| DE | 42 07 246 | 9/1993 |
| DE | 100 03 011 | 8/2000 |
| EP | 0 680 995 | 11/1995 |
| JP | 2003231810 | * 2/2003 |
| JP | 2003119622 | * 4/2003 |
| JP | 2003234013 | * 8/2003 |
| JP | 200327722 | * 11/2003 |
| WO | WO02/16257 | 2/2002 |

OTHER PUBLICATIONS

PCT/US02/27370 International Search Report (Nov. 11, 2002).

* cited by examiner

*Primary Examiner*—Katarzyna Wyrozebski
(74) *Attorney, Agent, or Firm*—Williams, Morgan & Amerson, P.C.

(57) ABSTRACT

The present invention relates to compositions comprising rigid-rod polymers and carbon nanotubes. The compositions comprise dispersed carbon nanotubes aligned with rigid-rod polymers. The alignment of the nanotubes and polymers can be liquid crystalline. The rigid-rod polymers of this invention include, but are not limited to, polymers and copolymers comprising benzobisazole, pyridobisimidazole and benzamidazobenzo-phenanthroline repeat units. Dispersion of carbon nanotubes is achieved by in-situ polymerization in the presence of the carbon nanotubes, which may be either single-wall or multi-wall or a combination of both. The polymer compositions comprising carbon nanotubes may be spun into fibers or formed into films. The strength of the resulting fibers of the present invention is significantly greater than that of fibers without carbon nanotubes.

83 Claims, 3 Drawing Sheets

“COMPOSITIONS COMPRISING RIGID-ROD POLYMERS AND CARBON NANOTUBES AND PROCESS FOR MAKING THE SAME

CROSS-REFERENCES TO RELATED APPLICATION

This application claims priority from U.S. provisional application, Ser. No. 60/315,583, filed Aug. 29, 2001, which application is incorporated herein by reference.

This invention was made with United States Government support under Grant No. F49620-00-1-0147 awarded by the United States Air Force. Government may have certain rights in the invention.

BACKGROUND OF THE INVENTION

Single-wall carbon nanotubes (SWNT) are fullerenes of closed-cage carbon molecules typically arranged in hexagons and pentagons. These carbon cylindrical structures, known commonly as "buckytubes", have extraordinary properties, including both high electrical and thermal conductivity, as well as high strength and stiffness. For background information on single-wall carbon nanotubes see B. I. Yakobson and R. E. Smalley, American Scientist, Vol. 85, July–August, 1997, pp. 324–337.

Nested single-wall carbon cylinders, known as multi-wall carbon nanotubes (MWNT), possess some properties similar to single-wall carbon nanotubes, however, since single-wall carbon nanotubes have fewer defects than multi-wall carbon nanotubes, the single-wall carbon nanotubes are generally stronger and more conductive.

To exploit the exceptional strength and conductive properties of carbon nanotubes, numerous attempts have been made to incorporate carbon nanotubes into polymers. However, one of the problems encountered in making polymer-nanotube composite blends is the difficulty in achieving a good dispersion of the nanotubes. The better the nanotube dispersion, the more the strength properties of the nanotubes will be conveyed to the polymer composite.

Carbon nanotubes, especially single-wall carbon nanotubes, once in contact, tend to be held tightly together by van der Waals forces. Dispersing single-wall carbon nanotubes is even more difficult than dispersing multi-wall nanotubes because the single-wall carbon nanotubes can "rope" together in aligned bundles of a few to many hundreds of nanotubes. In order to obtain a good nanotube dispersion, van der Waals forces which hold the nanotubes together must be overcome. Means to separate the nanotubes in intimate contact with each other, such as by sonication, can also damage the nanotubes and, consequently, impair strength and tensile properties.

Thus, there is a need for polymer composites comprising carbon nanotubes wherein the nanotubes are well dispersed in the polymer. There is also a need for high strength fibers for applications in articles such as bullet-proof vests, body armor, vehicular armor, ballistic protection equipment, and as reinforcing fibers for both organic and inorganic products, such as in tires, belts, ceramics, polymer laminates for aircraft and other compositions requiring high strength materials. Likewise, there is a need for a method for preparing polymer composites comprising carbon nanotubes wherein the carbon nanotubes are well-dispersed and wherein the structure and properties of the nanotubes have not been adversely affected.

SUMMARY OF THE INVENTION

The present invention relates to new polymer compositions comprising rigid-rod polymers and carbon nanotubes. The carbon nanotubes of this invention include both single-wall carbon nanotubes and multi-wall carbon nanotubes. Single-wall carbon nanotubes are considered to be the most rigid tubular polymeric material in existence with the highest tensile properties. (See B. I. Yakobson and R. E. Smalley, American Scientist, Vol. 85, July–August, 1997, pp. 324–337.)

Rigid-rod polymers are also characterized by high tensile strength, high modulus, stiffness and thermal stability. Such polymers are also referred to as liquid crystal extended chain polymers. Particularly useful are compositions comprising rigid-rod heterocyclic aromatic polymers and copolymers comprising benzobisazole, pyridobisazole and/or benzamidazobenzophenanthroline repeat units. In this application, rigid-rod polymers shall be defined as those polymers comprising benzobisazole, pyridobisazole and/or benzamidazobenzophenanthroline repeat units, and shall include copolymers, comprising at least one different monomer repeat unit, and substituted polymers and copolymers, wherein other chemical moieties or functional groups are substituted on the benzobisazole, pyridobisazole and/or benzamidazobenzophenanthroline repeat units.

This invention also relates to a method of forming polymer composites comprising well-dispersed carbon nanotubes by in-situ polymerizing a rigid-rod polymer or copolymer in the presence of carbon nanotubes. In the polymerization, rigid-rod polymers or copolymers are formed and generally align in an anisotropic, liquid crystal distribution. The propagating rigid-rod polymer or copolymer acts as a template for ordering the carbon nanotubes. As the rigid-rod polymer or copolymer orders into liquid crystalline domains, the polymer or copolymer entraps the carbon nanotubes in the liquid crystalline solution or dope. These polymer-nanotube compositions are extremely suitable for spinning into highly ordered and high strength fibers which exhibit significantly improved tensile properties over fibers spun without nanotubes. Likewise, formation of composite rigid-rod polymer/nanotube films also results in films with significantly improved strength properties over the films without nanotubes.

DESCRIPTION OF ILLUSTRATIVE EMBODIMENTS

Figure 1:
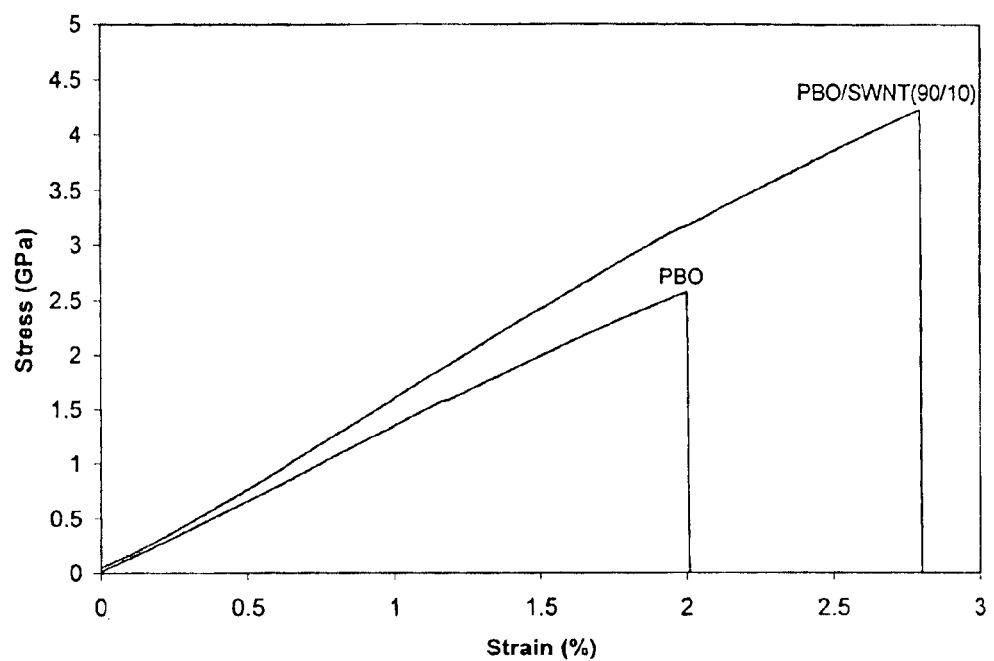
FIG. 1 shows typical stress-strain curves for PBO and PBO/SWNT (90/10) fibers.

This invention provides a composition comprising a dispersion of carbon nanotubes in rigid-rod polymers or copolymers. In the scope of this invention, the term "polymers" shall also include "copolymers". The invention also provides a method for producing polymer compositions comprising carbon nanotubes and rigid-rod polymers and copolymers. The method involves in-situ polymerization of rigid-rod polymers in the presence of carbon nanotubes. The carbon nanotubes may be either single-wall, multi-wall or a combination thereof. The in-situ polymerization is done through the polycondensation of diamines and diacid monomers in the presence of carbon nanotubes. As the rigid-rod polymers or copolymers polymerize, liquid crystalline domains form. The nanotubes align along the propagating para-ordered rigid-rod molecules and are entrapped in the resulting dope. The resulting anisotropic alignment of the rigid-rod polymers and carbon nanotubes appears liquid crystalline in nature. The present invention provides a substantially uniform, aligned distribution of nanotubes that is not readily obtainable by the process of melt mixing a molten polymer with carbon nanotubes.

Processing of the new compositions into fibers and films provides hybrid materials with vastly improved tensile properties, which are superior to the same polymers without incorporated nanotubes. Although not meaning to be limited, the polymer component of the present compositions can include various benzobisazole, pyridobisimidazole, and benzamidazobenzophenanthroline polymers and copolymers. Fibers of these polymers and copolymers are known for their extremely high modulus and high strength. Rigid rod polymers and copolymers based on benzobisazole include the repeating group:

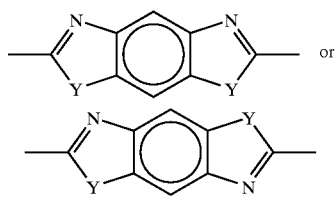

where Y is —O—, —S— or —NR', where R' is —H, alkyl having 1 to 4 carbon atoms, or an aromatic group having 1 or 2 aromatic rings.

Examples of rigid-rod benzobisazole polymers include para-ordered heterocyclic polymer having a repeat group of the formula

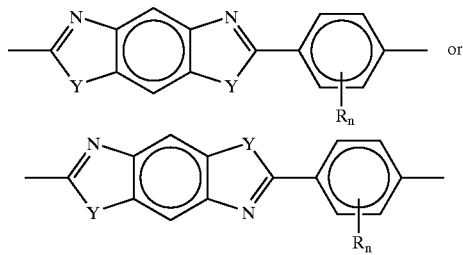

wherein Y is —S—, n is 1 or 2, and R is a hydroxyl group, a sulfo group or an alkyl group having 1 to 4 carbon atoms.

Other examples of rigid rod polymers include benzimidazole polymers and copolymers comprising repeat units of the formula

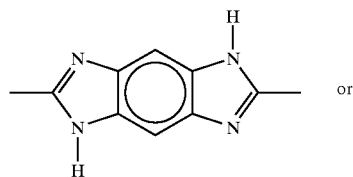

-continued

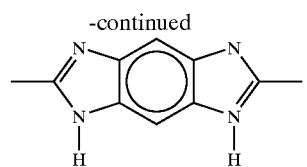

and include p-phenylenebenzimidazole (PBI) comprising repeat units of the formula

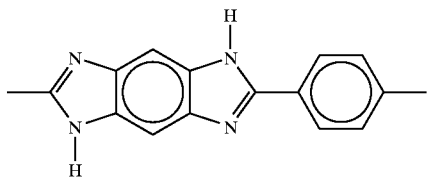

Such polymers and copolymers are described in U.S. Pat. No. 3,901,855 and incorporated by reference herein in its entirety. Further examples of benzobisazole polymers are polybenzobisoxazole polymers and copolymers comprising repeat units of the formula

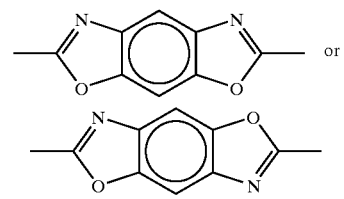

and include polymers and copolymers of p-phenylenebenzobisoxazole (PBO) comprising repeat units of the formula

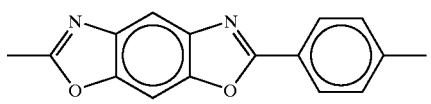

Further examples of benzobisazole polymers include polymers and copolymers of polybenzobisthiazole comprising repeat units of the formula

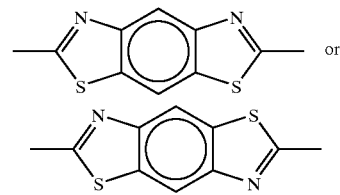

and include polymers and copolymers of p-phenylenebenzobisthiazole (PBZT) comprising repeat units of the formula

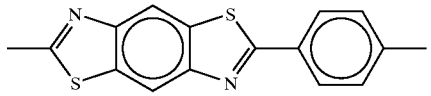

both described in U.S. Pat. No. 4,533,693, incorporated by reference herein in its entirety. Further examples of benzobisazole polymers and copolymers are those p-phenylenebenzobisazole polymers and copolymers containing pendant substituents on the phenylene group, including phenylenebenzobisazoles with pendant hydroxyl groups, such as dihydroxyphenylene-benzobisoxazole (Di—OH PBO), comprising repeat units of the formula

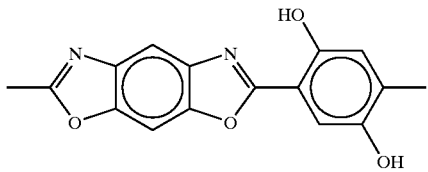

dihydroxy-phenylenebenzobisimidazole (Di—OH PBI) comprising repeat units of the formula

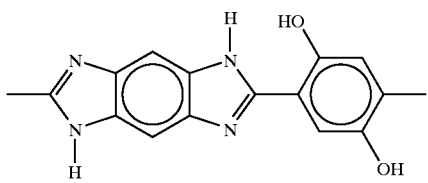

dihydroxyphenylenebenzobisthiazole (Di—OH PBZT), comprising repeat units of the formula

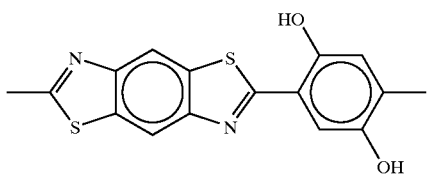

described in U.S. Pat. Nos. 5,041,522 and 5,039,778, each incorporated by reference herein in its entirety, and dihydroxyphenylenepyridobisimidazole (Di—OH PPBI) comprising repeat units of the formula

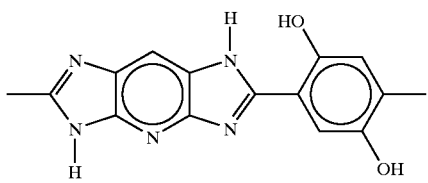

and described in U.S. Pat. No. 5,674,969, incorporated by reference herein in its entirety, polymers and copolymers of phenylenebenzobisazoles having pendant sulfo groups, such as sulfo-phenylenebenzobisoxazole (sulfo-PBO) comprising repeat units of the formula

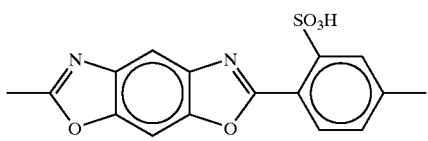

sulfopolybenzobisimidazole (sulfo-PBI), comprising repeat units of the formula

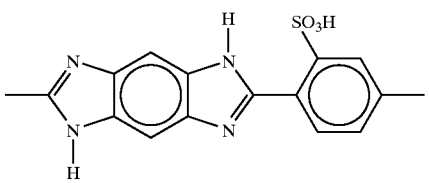

and sulfo-phenylenebenzobisthiazole (sulfo-PBZT), comprising repeat units of the formula

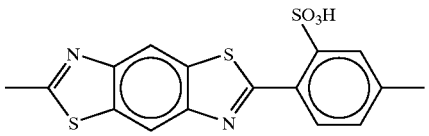

described in U.S. Pat. Nos. 5,312,876 and 5,312,895, each incorporated by reference herein in its entirety, polymers and copolymers phenylenebenzobisazole with pendant methyl groups, such as methyl- and dimethylphenylenebenzobisoxazole (Me-PBO) comprising repeat units of the formula

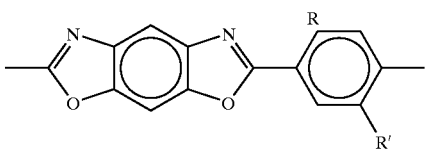

where R and R'=$CH_3$ or where R=$CH_3$ and R'=H methyl- and dimethyl-phenylenebenzobisimidazole (Me—PBI), comprising repeat units of the formula

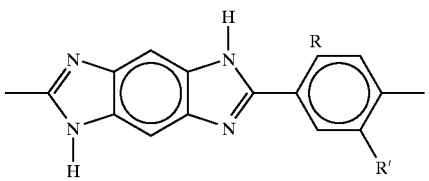

where R and R'=$CH_3$ or where R=$CH_3$ and R'=H and methyl- and dimethyl-phenylenebenzobisthiazole (Me-PBZT), comprising repeat units of the formula

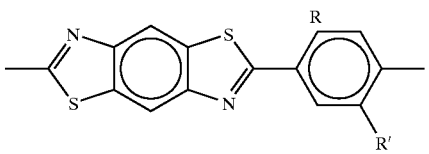

where R and R'=$CH_3$ or where R=$CH_3$ and R'=H described in U.S. Pat. Nos. 5,000,217, 5,098,988 and 5,136,012, each incorporated by reference herein in its entirety. Another example of rigid rod polymers include polymers and copolymers of benzamidazobenzophenanthroline (BBL) comprising repeat units of the formula

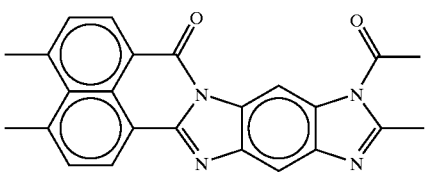

described in U.S. Pat. No. 3,632,414, incorporated by reference herein in its entirety.

In this invention, the rigid rod polymers and copolymers, such as those based on benzobisazoles, pyridobisazoles and benzamidazobenzophenanthroline, are formed in-situ from the polycondensation of diamine and diacid monomers. Suitable amino-group-containing monomers include, but are not limited to: 2,5-diamino-1,4-benzenedithiol dihydrochloride, 4,6-diamino-1,3-benzenediol dihydrochloride, 1,2,4,5-tetraaminobenzene tetrahydrochloride, 2,3,5,6-tetraaminopyridine tetrahydrochloride, 2,5-diamino-1,4-benzenediol dihydrochloride, and 1,4,5,8-tetraaminonaphthalene tetrahydrochloride. Suitable acid-group-containing monomers include, but are not limited to: terephthalic acid, mono- and dihydroxy-terephthalic acid, 2-sulfoterephthalic acid, 1,4,5,8-tetracarboxynaphthalene, 2-methylterephthalic acid, 2,5-dimethyl-terephthalic acid, 1,5-dicarboxynaphthalene, and 2,6-dicarboxynaphthalene.

The in-situ polymerizations may be conducted in any suitable medium in which the rigid-rod polymers can be formed and maintained in solution. A suitable medium for carrying out the polycondensation polymerizations of the present invention comprises polyphosphoric acid (PPA), having a formula represented by $H_{n+2}P_nO_{3n+1}$ or HO—$(PO_3H)_n$—H. The polyphosphoric acid composition can be expressed in terms of the phosphorous pentoxide ($P_2O_5$) content or the phosphoric acid ($H_3PO_4$, n=1) content.

The polymer concentration in the medium preferably is selected to promote the formation of an anisotropic reaction mixture. Polymer concentrations in the range from about 1 wt % to about 20 wt % in the medium can promote an anisotropic reaction mixture. The carbon nanotube concentration preferably can range from about 0.1 wt % to about 50 wt %, more preferably from about 1 wt % to about 30 wt % based on the weight of polymer in the polymerization.

In the present invention, the process for making a rigid-rod polymer/nanotube composition involves synthesizing the rigid-rod polymer or copolymer in the presence of carbon nanotubes. In one embodiment of in-situ polymerization, stoichiometric amounts of amine hydrochloride and acid monomers are combined in 85% phosphoric acid and heated to a temperature in the range of about 60° to about 80° C. to effect the thermal dehydrochlorination of the amine monomer. Note that the use of amines without protective hydrochloride is also within the scope of this invention. After the dehydrochlorination is complete, the nanotubes are added. The temperature is then raised to about 100° C. and maintained for about 4 to 6 hours. The reaction temperature is cooled to about 45° C. and phosphorous pentoxide ($P_2O_5$) is added to make 77% PPA. After the phosphorous pentoxide addition, the temperature is increased to 100° C. and maintained for about 4 hours. Additional $P_2O_5$ is then added to increase the PPA concentration to about 82 to about 84% PPA. The temperature is then raised to about 165° C. and maintained at that temperature for about 10 to 12 hours. The temperature of the reaction mixture is then raised to about 190° C. and held for about 4 hours. The procedure results in a liquid crystalline composition comprising rigid-rod liquid crystalline polymer and nanotubes that can be extruded and processed into fiber or film.

After each in-situ polymerization, aliquot samples are taken to determine intrinsic viscosity and also for processing into cast films. The samples are precipitated into water, treated with ammonium hydroxide, washed extensively with water, and dried under reduced pressure. After precipitating into water or redissolving of dried samples in methanesulfonic acid for intrinsic viscosity measurements, the samples show no separation of the nanotubes from the derived polymer.

Fiber spinning may be done by any suitable technique. One such method is dry-jet wet spinning using a piston driven spinning system. For fiber spinning, the polymer solution or dope comprising the rigid-rod polymer, nanotubes and phosphoric acid medium preferably is maintained between about 100° C. and about 150° C. An air gap preferably is maintained in the range of about 2 cm and about 25 cm. Extruded fiber is coagulated in water at room temperature. Fiber is washed in running water for about a week or for any time sufficient to remove the acid from the fiber. The fiber is subsequently dried in vacuum at about 80° C. Dried fiber can be heat-treated in nitrogen at about 400° C. to impart higher strength and tensile properties. Generally, the fibers of the present invention comprising rigid-rod polymer/carbon nanotube composites have significantly higher strength and tensile properties, such as higher stiffness, tensile modulus, and strain to failure (elongation to break), than like polymer fibers without nanotubes. Certain fibers comprising the rigid-rod polymers/nanotube composites of this invention have shown about 50% greater tensile strength than over fibers of the same polymeric composition without nanotubes. Fibers prepared with the compositions of this invention also show lower creep than like polymer fibers without carbon nanotubes.

This composite of this invention provides a fundamental improvement in products and articles of manufacture comprising rigid-rod polymers and copolymers, and it enables new and improved articles of manufacture, including, but not limited to composite structural materials, films, coatings and fibers requiring high tensile strength such as for high-strength fibers and structural elements of machines, buildings, and vehicles. Improved articles of manufacture incorporating fibers of the present invention include body armor, bullet-proof vests, vehicular armor, armor for structures, elements of ballistic protection systems and as reinforcing fibers for both organic and inorganic products, such as in tires, belts, ceramics, polymer laminates for aircraft and other compositions requiring high strength materials. Depending on the nanotube concentration and dispersion, additional properties of electrical or thermal conductivity, electromagnetic and radio-frequency shielding may also be realized.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

PBZT/SWNT (95/5)

A composition of 5% single-wall carbon nanotubes (SWNT) and 95% polyphenylenebenzobisthiazole (PBZT) was prepared as follows. Into the bottom of a 250-ml resin flask equipped with a mechanical stirrer, a nitrogen inlet and outlet, was placed 4.904 g (0.02 mol) of 2,5-diamino-1,4-benzenedithiol dihydrochloride, 3.3226 g (0.02 mol) of terephthalic acid, and 20.68 g of phosphoric acid (85%). The resulting mixture was dehydrochlorinated under nitrogen atmosphere at 65° C. for 16 hours. The temperature was then raised to 80° C. and held for 4 hours. 0.26 g of purified single-wall carbon nanotubes (HiPco™ single-wall carbon nanotubes from Carbon Nanotechnologies, Inc., Houston, Tex., purified according to the procedures given in I. W. Chiang, et al., *J. Phys. Chem.*, Vol. 105, 2001, p. 8297) was added to the mixture and heated at 100° C. for 16 hours. The mixture was then cooled the mixture to room temperature. 13.69 g $P_2O_5$ was added to the mixture to generate polyphosphoric acid (77% $P_2O_5$). The mixture was stirred for 2 hours at 80° C. and cooled to room temperature. 12.13 g of $P_2O_5$ was added to the mixture to bring the polymer concentration to 10%. The mixture was heated at 160° C. for 16 hours. As the temperature increased, stir opalescence began to occur at about 150° C. The mixture was finally heated to 190° C. for an additional 4 hours. An aliquot of the polymer dope was precipitated in water, broken up with a blender, collected by suction filtration, washed with water and dried under reduced pressure (0.02 mm Hg) at 100° C. for 24 hours. An intrinsic viscosity of 17 dl/g was determined in methanesulfonic acid at 30° C.

EXAMPLE II

PBZT/MWNT (90/10)

A composition of 10% multi-wall carbon nanotubes (MWNT) and 90% polyphenylenebenzobisthiazole (PBZT) was prepared as follows. Into the bottom of a 250-ml resin flask equipped with a mechanical stirrer, a nitrogen inlet and outlet, was placed 4.904 g (0.02 mol) of 2,5-diamino-1,4-benzenedithiol dihydrochloride, 3.3226 g (0.02 mol) of terephthalic acid, and 20.68 g of phosphoric acid (85%). The resulting mixture was dehydrochlorinated under nitrogen atmosphere at 65° C. for 16 hours. The temperature was then raised to 80° C. and held for 4 hours. 0.52 g of multi-wall carbon nanotubes (Pyrograph PR-24-HT carbon nanofiber grade from Applied Sciences, Inc., Cedarville, Ohio) was added to the mixture. The mixture was heated at 100° C. for 16 hours and then cooled to room temperature. 13.69 g $P_2O_5$ was added to the mixture to generate polyphosphoric acid (77% $P_2O_5$). The mixture was stirred for 2 hours at 80° C. and then cooled to room temperature. 12.13 g of $P_2O_5$ was added to the mixture to bring the polymer concentration to 10%. The mixture was heated at 160° C. for 16 hours. As the temperature increased, stir opalescence began to occur at about 150° C. The mixture was finally heated to 190° C. and held for an additional 4 hours. An aliquot of the polymer dope was precipitated in water, broken up with a blender, collected by suction filtration, washed with water and dried under reduced pressure (0.02 mmHg) at 100° C. for 24 hours. An intrinsic viscosity of 28 dl/g was determined in methanesulfonic acid at 30° C.

EXAMPLE III

PBO/SWNT (95/5)

A composition of 5% single-wall carbon nanotubes (SWNT) and 95% polyphenylenebenzobisoxazole (PBO) was prepared as follows. Into the bottom of a 250-ml resin flask equipped with a mechanical stirrer, a nitrogen inlet and outlet, was place 4.2612 g (0.02 mol) of 1,4-diaminoresorcinol dihydrochloride, 4.0605 g (0.02 mol) of terephthaloyl chloride, and 12.14 g of phosphoric acid (85%). The resulting mixture was dehydrochlorinated under nitrogen atmosphere at 65° C. for 16 hours. The temperature was then raised to 80° C. and held for 4 hours. 0.234 g of purified single-wall carbon nanotubes (HiPco™ single-wall carbon nanotubes from Carbon Nanotechnologies, Inc., Houston, Tex., purified according to the procedures given in I. W. Chiang, et al., *J. Phys. Chem.*, Vol. 105, 2001, p. 8297) was added to the mixture. The mixture was heated at 100° C. for 16 hours and then cooled to room temperature. 8.04 g of $P_2O_5$ was added to the mixture to generate polyphosphoric acid (77% $P_2O_5$). The mixture was stirred for 2 hours at 80° C. and then cooled to room temperature. 7.15 g of $P_2O_5$ was added to the mixture to bring the polymer concentration to 14%. The mixture was heated at 160° C. for 16 hours. As the temperature increased, stir opalescence began to occur at about 155° C. The mixture was finally heated to 190° C. for an additional 4 hours. An aliquot of the polymer dope was precipitated in water, broken up with a blender, collected by suction filtration, washed with water and dried under reduced pressure (0.02 mmHg) at 100° C. for 24 hours. An intrinsic viscosity of 14 dl/g was determined in methanesulfonic acid, at 30° C.

EXAMPLE IV

PBO/SWNT (90/10)

A composition of 10% single-wall carbon nanotubes (SWNT) and 90% polyphenylenebenzobisoxazole (PBO) was prepared as follows. Into the bottom of a 250-ml resin flask equipped with a mechanical stirrer, a nitrogen inlet and outlet, was placed 4.2612 g (0.02 mol) of 1,4-diaminoresorcinol dihydrochloride, 4.0605 g (0.02 mol) of terephthaloyl chloride, and 12.14 g of phosphoric acid (85%). The resulting mixture was dehydrochlorinated under nitrogen atmosphere at 65° C. for 16 hours. The temperature was then raised to 80° C. and held for 4 hours. 0.47 g of purified SWNT (HiPco™ single-wall carbon nanotubes from Carbon Nanotechnologies, Inc., Houston, Tex., purified according to the procedures given in I. W. Chiang, et al., *J. Phys. Chem.*, Vol. 105, 2001, p. 8297) tubes was added to the mixture. The mixture was heated at 100° C. for 16 hours and then cooled the mixture to room temperature. 8.04 g of $P_2O_5$ was added to the mixture to generate polyphosphoric acid (77% $P_2O_5$). The mixture was stirred for 2 hours at 80° C. and then cooled to room temperature. 7.15 g of $P_2O_5$ was added to the mixture to bring the polymer concentration to 14%. The mixture was heated at 160° C. for 16 hours. As the temperature increased, stir opalescence began to occur at about 155° C. The mixture was finally heated to 190° C. and held for an additional 4 hours.

No SWNT aggregates were observed in optical micrographs taken of the PBO/SNWT dope under cross polarizers, indicating good nanotube dispersion at the optical scale during PBO polymerization. An aliquot of the polymer dope was precipitated in water, broken up with a blender, collected by suction filtration, washed with water and dried under reduced pressure (0.02 mmHg) at 100° C. for 24 hours. An intrinsic viscosity of 14 dl/g was determined in methanesulfonic acid, at 30° C.

EXAMPLE V

PBO/SWNT (80/20)

A composition of 20% single-wall carbon nanotubes (SWNT) and 80% polyphenylenebenzobisoxazole (PBO) was prepared as follows. Into the bottom of a 250-ml resin flask equipped with a mechanical stirrer, a nitrogen inlet and outlet, was placed 4.2612 g (0.02 mol) of 1,4-diaminoresorcinol dihydrochloride, 4.0605 g (0.02 mol) of terephthaloyl chloride, and 16.87 g of phosphoric acid (85%). The resulting mixture was dehydrochlorinated under nitrogen atmosphere at 65° C. for 16 hours. The temperature was then raised to 80° C. and held for 4 hours. 0.94 g of purified SWNT (HiPco™ single-wall carbon nanotubes from Carbon Nanotechnologies, Inc., Houston, Tex., purified according to the procedures given in I. W. Chiang, et al., *J. Phys. Chem.*, Vol. 105, 2001, p. 8297) was added to the mixture. The mixture was heated at 100° C. for 16 hours and then cooled to room temperature. 11.16 g of $P_2O_5$ was added to the mixture to generate polyphosphoric acid (77% $P_2O_5$). The mixture was stirred for 2 hours at 80° C. and then cooled to room temperature. 13.4 g of $P_2O_5$ was added to the mixture to bring the polymer concentration to 10%. The mixture was heated at 160° C. for 16 hours. As the temperature increased, stir opalescence began to occur at about 155° C. The mixture was finally heated to 190° C. and held for an additional 4 hours. An aliquot of the polymer dope was precipitated in water, broken up with a blender, collected by suction filtration, washed with water and dried under reduced pressure (0.02 mmHg) at 100° C. for 24 hours. An intrinsic viscosity of 13 dl/g was determined in methanesulfonic acid, at 30° C.

EXAMPLE VI

PBO Control

Polyphenylenebenzobisoxazole (PBO) was prepared as follows. Into the bottom of a 250-ml resin flask equipped with a mechanical stirrer, a nitrogen inlet and outlet, was placed 4.2612 g (0.02 mol) of 1,4-diaminoresorcinol dihydrochloride, 4.0605 g (0.02 mol) of terephthaloyl chloride, and 16.87 g of phosphoric acid (85%). The resulting mixture was dehydrochlorinated under nitrogen atmosphere at 65° C. for 16 hours. The temperature was then raised to 80° C. and held for 4 hours. The mixture was then heated at 100° C. for 16 hours and then cooled to room temperature. 11.16 g of $P_2O_5$ was added to generate polyphosphoric acid (77% $P_2O_5$). The mixture was stirred for 2 hours at 80° C. and cooled to room temperature. 13.4 g of $P_2O_5$ was added to bring the polymer concentration to 10%. The polymer mixture was heated at 160° C. for 16 hours. As the temperature increased, stir opalescence began to occur at about 155° C. The mixture was finally heated to 190° C. and held for an additional 4 hours. An aliquot of the polymer dope was precipitated in water, broken up with a blender, collected by suction filtration, washed with water and dried under reduced pressure (0.02 mmHg) at 100° C. for 24 hours. An intrinsic viscosity of 12 dl/g was determined in methanesulfonic acid at 30° C.

EXAMPLE VII

Di—OH—PPBI/MWNT (95/5)

A composition of 5% multi-wall carbon nanotubes (MWNT) and 95% polydihydroxyphenylenepyridobisimidazole (Di—OH—PPBI) was prepared as follows. Into the bottom of a 250-ml resin flask equipped with a mechanical stirrer, a nitrogen inlet and outlet, was placed 5.3310 g (0.02 mol) of 2,3,5,6-tetraaminopyridine-trihydrochloride-monohydrate, 4.7004 g (0.02 mol) of 2,5-dihydroxyterephthaloyl chloride, and 11.66 g of phosphoric acid (85%). The resulting mixture was dehydrochlorinated under nitrogen atmosphere at 65° C. for 16 hours. The temperature was then raised to 80° C. and held for 4 hours. 0.26 g of multi-wall carbon nanotubes (Pyrograph PR-24-HT carbon nanofiber grade from Applied Sciences, Inc., Cedarville, Ohio) was added to the mixture. The mixture was heated at 100° C. for 16 hours and then cooled to room temperature. 7.71 g of $P_2O_5$ was added to the mixture to generate polyphosphoric acid (77% $P_2O_5$). The mixture was stirred for 2 hours at 80° C. and then cooled to room temperature. 12.14 g of $P_2O_5$ was added to the mixture to bring the polymer concentration to 14%. The mixture was heated at 165° C. for 16 hours. As the temperature increased, stir opalescence began to occur at about 158° C. The mixture was finally heated to 190° C. and held for an additional 4 hours. An aliquot of the polymer dope was precipitated in water, broken up with a blender, collected by suction filtration, washed with water and dried under reduced pressure (0.02 mmHg) at 100° C. for 24 hours. An intrinsic viscosity of 18 dl/g was determined in methanesulfonic acid at 30° C.

EXAMPLE VIII

Di—OH—PPBI/SWNT (95/5)

A composition of 5% single-wall carbon nanotubes (SWNT) and 95% polydihydroxyphenylenepyridobisimidazole (Di—OH—PPBI) was prepared as follows. Into the bottom of a 250-ml resin flask equipped with a mechanical stirrer and a nitrogen inlet/outlet, was placed 5.3310 g (0.02 mol) of 2,3,5,6-tetraaminopyridine-trihydrochloride-monohydrate, 4.7004 g (0.02 mol) of 2,5-dihydroxyterephthaloyl chloride, and 11.66 g of phosphoric acid (85%). The resulting mixture was dehydrochlorinated under nitrogen atmosphere at 65° C. for 16 hours. The temperature was then raised to 80° C. and held for 4 hours. 0.26 g of purified SWNT (HiPco™ single-wall carbon nanotubes from Carbon Nanotechnologies, Inc., Houston, Tex., purified according to the procedures given in I. W. Chiang, et al., *J. Phys. Chem.*, Vol. 105, 2001, p. 8297) was added to the mixture. The mixture was heated at 100° C. for 16 hours and then cooled to room temperature. 7.71 g of $P_2O_5$ was added to the mixture to generate polyphosphoric acid (77% $P_2O_5$). The mixture was then stirred for 2 hours at 80° C. and cooled to room temperature. 12.14 g of $P_2O_5$ was added to the mixture to bring the polymer concentration to 14%. The mixture was then heated at 165° C. for 16 hours. As the temperature increased, stir opalescence began to occur at about 158° C. The mixture was finally heated to 190° C. and held for an additional 4 hours. An aliquot of the polymer dope was precipitated in water, broken up with a blender, collected by suction filtration, washed with water and dried under reduced pressure (0.02 mmHg) at 100° C. for 24 hours. An intrinsic viscosity of 17 dl/g was determined in methanesulfonic acid at 30° C.

EXAMPLE IX

DIOH—PBI/MWNT (95/5)

A composition of 5% multi-wall carbon nanotubes (MWNT) and 95% polydihydroxyphenylenebenzo-bisimidazole (Di—OH—PBI) was prepared as follows. Into the bottom of a 250-ml resin flask equipped with a mechanical stirrer, a nitrogen inlet and outlet, was placed 5.6804 g (0.02 mol) of 1,2,4,5-tetraaminobenzene tetrahydrochloride, 4.7004 g (0.02 mol) of 2,5-dihydroxyterephthaloyl chloride, and 12.55 g of phosphoric acid (85%). The resulting mixture was dehydrochlorinated under nitrogen atmosphere at 65° C. for 16 hours. The temperature was then raised to 80° C. and held for 4 hours. 0.26 g MWNT (Pyrograph PR-24-HT carbon nanofiber grade from Applied Sciences, Inc., Cedarville, Ohio) was added to the mixture. The mixture was heated at 100° C. for 16 hours and then cooled to room temperature. 8.30 g of $P_2O_5$ was added to the mixture to generate polyphosphoric acid (77% $P_2O_5$). The mixture was stirred for 2 hours at 80° C. and then cooled to room temperature. 10.89 g of $P_2O_5$ was added to the mixture to bring the polymer concentration to 14%. The mixture was heated at 145° C. for 36 hours. As the temperature increased, stir opalescence began to occur at about 140° C. An aliquot of the polymer dope was precipitated in water, broken up with a blender, collected by suction filtration, washed with water and dried under reduced pressure (0.02 mmHg) at 100° C. for 24 hours. An intrinsic viscosity of 17.5 dl/g was determined in methanesulfonic acid at 30° C.

EXAMPLE X

BBL/MWNT (95/5)

A composition of 5% multi-wall carbon nanotubes (MWNT) and 95% ladder polymer benzimidazobenzophenanthroline (BBL) was prepared as follows. Into the bottom of a 250-ml resin flask equipped with a mechanical stirrer, a nitrogen inlet and outlet, was placed 5.6804 g (0.02 mol) of 1,2,4,5-tetraaminobenzene tetrahydrochloride, 6.0842 g (0.02 mol) of 1,4,5,8-naphthalenetetracarboxylic acid, and 16.16 g of phosphoric acid (85%). The resulting mixture was dehydrochlorinated under nitrogen atmosphere at 65° C. for 16 hours. The temperature was then raised to 80° C. and held for 4 hours. 0.33 g of multi-wall carbon nanotubes (Pyrograph PR-24-HT carbon nanofiber grade from Applied Sciences, Inc., Cedarville, Ohio) was added to the mixture. The mixture was heated at 100° C. for 16 hours and then cooled to room temperature. 10.69 g of $P_2O_5$ was added to the mixture to generate polyphosphoric acid (77% $P_2O_5$). The mixture was stirred for 2 hours at 80° C. and cooled to room temperature. 20.02 g of $P_2O_5$ was added to the mixture to bring the polymer concentration to 12%. The mixture was then heated at 160° C. for 16 hours. As the temperature increased, stir opalescence began to occur at about 160° C. The mixture was finally heated to 190° C. and held for additional 4 hours. An aliquot of the polymer dope was precipitated in water, broken up with a blender, collected by suction filtration, washed with water and dried under reduced pressure (0.02 mmHg) at 100° C. for 24 hours. An intrinsic viscosity of 20 dl/g was determined in methanesulfonic acid at 30° C.

EXAMPLE XI

PBO/SWNT (95/5) Fiber Formation

Fibers of the polymer composition of 5% single-wall carbon nanotubes (SWNT) and 95% polyphenylenebenzobisoxazole (PBO), as made by the procedure in Example III, were dry-jet wet spun using a piston driven spinning system manufactured by Bradford University Research Ltd. The polymer dope was first preheated to 50° C. for about 15 minutes. The polymer dope was then formed into a cylindrical shape under dry nitrogen and transferred to the spinning cylinder. The polymer composition was heated at 100° C. for about five hours before spinning. A 50-μm stainless steel filter (from Anderson Wire Works, Inc.) filter was used in-line for fiber spinning and the spinneret diameter was 250 μm. A 30-mm spinning cylinder was used with a 28-mm diameter piston. The length of the air gap was 10 cm and length of the coagulation bath was 75 cm. Spun fiber was washed in water for one week, vacuum dried at 80° C. for 12 hours and subsequently heat-treated in a Thermolyne 21100 tube furnace at 400° C. in nitrogen under tension for 2 minutes.

EXAMPLE XII

PBO/SWNT (90/10) Fiber Formation

Fiber formation with the polymer composition of 10% single-wall carbon nanotubes (SWNT) and 90% polyphenylenebenzobisoxazole (PBO), as made by the procedure in Example IV, was tried at different temperatures using dry-jet wet spinning with a piston driven spinning system manufactured by Bradford University Research Ltd. The polymer dope was heated to 100° C. Fiber could not be spun at this temperature because the thrust was too high. Attempts were also made to spin the fiber at 120° C. as well as 130° C. Successful fiber spinning was conducted at 150° C. using dry-jet wet spinning. A 50-μm stainless steel filter (from Anderson Wire Works, Inc.) was used in-line for fiber spinning and the spinneret diameter was 250 μm. 30 mm spinning cylinder was used with a 28-mm diameter piston. The length of the air gap was 10 cm and length of the coagulation bath was 75 cm. Spun fiber was washed in water for one week, vacuum dried at 80° C. for 12 hours and subsequently heat-treated in a Thermolyne 21100 tube furnace in nitrogen at 400° C. under tension for 2 minutes.

EXAMPLE XIII

PBO Control Fiber Formation

Fibers of polyphenylenebenzobisoxazole (PBO), as made by the procedure in Example VI, were dry-jet wet spun using a piston driven spinning system manufactured by Bradford University Research Ltd. The polymer dope was first preheated to 50° C. for about 15 minutes. The polymer dope was then formed into a cylindrical shape under dry nitrogen and transferred to the spinning cylinder. The polymer was heated at 100° C. for about five hours before spinning. A 50-μm stainless steel filter (from Anderson Wire Works, Inc.) was used in-line for fiber spinning and the spinneret diameter was 250 μm. A 30-mm spinning cylinder was used with a 28-mm diameter piston. The length of the air gap was 10 cm and length of the coagulation bath was 75 cm. Spun fiber was washed in water for one week, vacuum dried at 80° C. for 12 hours and subsequently heat-treated in a Thermolyne 21100 tube furnace at 400° C. in nitrogen under tension for 2 minutes.

EXAMPLE XIV

Fiber Testing

Tensile modulus, tensile strength, and elongation to break were determined for the PBO-based fibers prepared according to Examples XI, XII and XIII, 95/5 PBO/SWNT, 90/10 PBO/SWNT and PBO control, respectively. The fibers were mounted on cardboard tabs. Tensile testing was performed on an Instron Universal Tensile Tester (Model 5567) at 2.54 cm gauge length at a strain rate of 2% per minute. Fiber diameters were measured using laser diffraction. About 20 samples of each fiber were tested. The data are given in Table 1.

TABLE 1

Mechanical Properties of PBO and PBO/SWNT composite fibers.

| First Example | Tensile Modulus (GPa) | Tensile Strength (GPa) | Elongation to Break (%) |
|---|---|---|---|
| PBO Control (Example XIII) | 138 | 2.6 | 2.0 |
| PBO/SWNT (95/5) (Example XI) | 156 | 3.2 | 2.3 |

TABLE 1-continued

Mechanical Properties of PBO and PBO/SWNT composite fibers.

| First Example | Tensile Modulus (GPa) | Tensile Strength (GPa) | Elongation to Break (%) |
|---|---|---|---|
| PBO/SWNT (90/10) (Example XII) | 167 | 4.2 | 2.8 |

The data show that tensile modulus, tensile strength, as well as elongation to break of PBO/SWNT (90/10) fiber are all higher than comparable measurements for the control PBO fiber by about 20, 60, and 40%, respectively. The average tensile strength values for the PBO control fibers varied between 1.8 and 2.6 GPa, while the average tensile strength values for the PBO/SWNT (90/10) fibers varied between 2.9 and 4.2. Thus, for various trials, a tensile strength increase of 40 to 60% was obtained by incorporating 10 wt % SWNT in PBO. The stress-strain curves for PBO/SWNT (90/10) and PBO control fibers are shown in FIG. 1.

Figure 2:
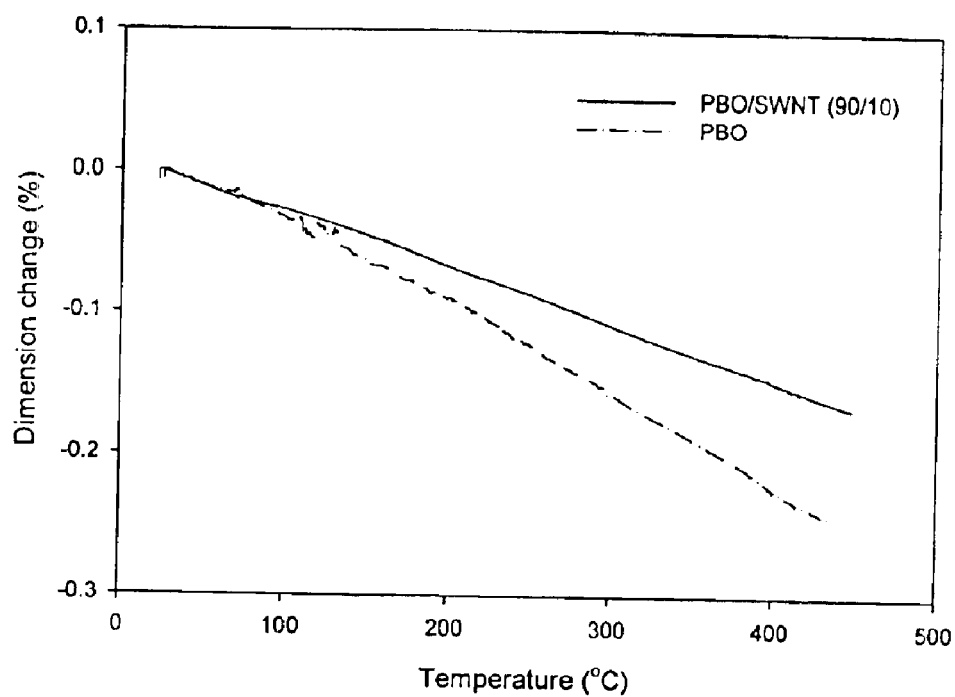
FIG. 2 shows thermal shrinkage at 25 MPa stress in PBO and PBO/SWNT (90/10) fibers when heated at 10° C. per minute in nitrogen
Figure 3:
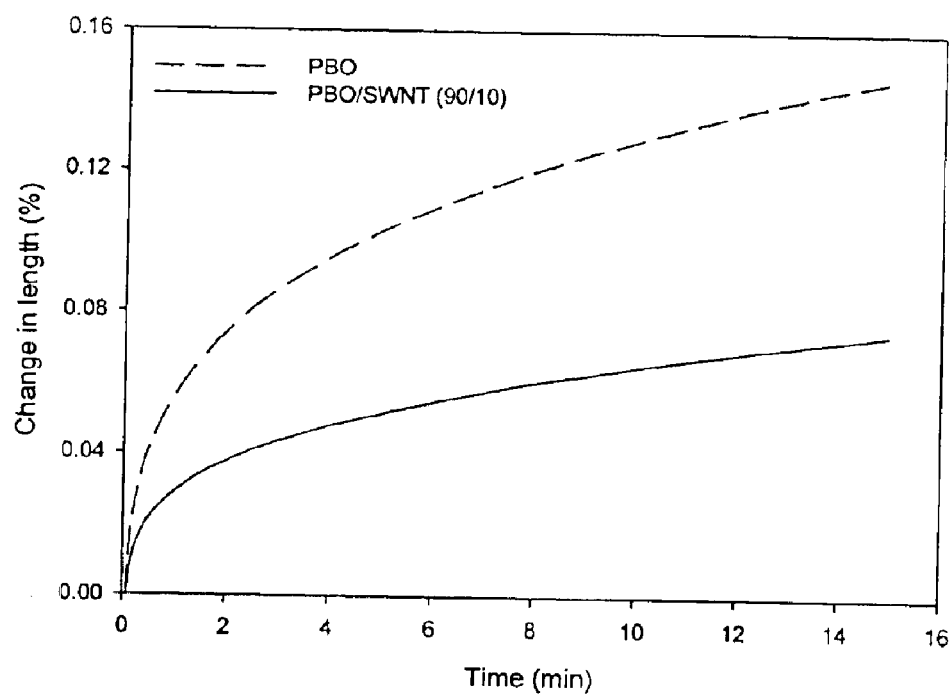
FIG. 3 shows creep behavior of PBO and PBO/SWNT (90/10) fibers at 400° C. at a stress of 250 MPa.
Figure 4:
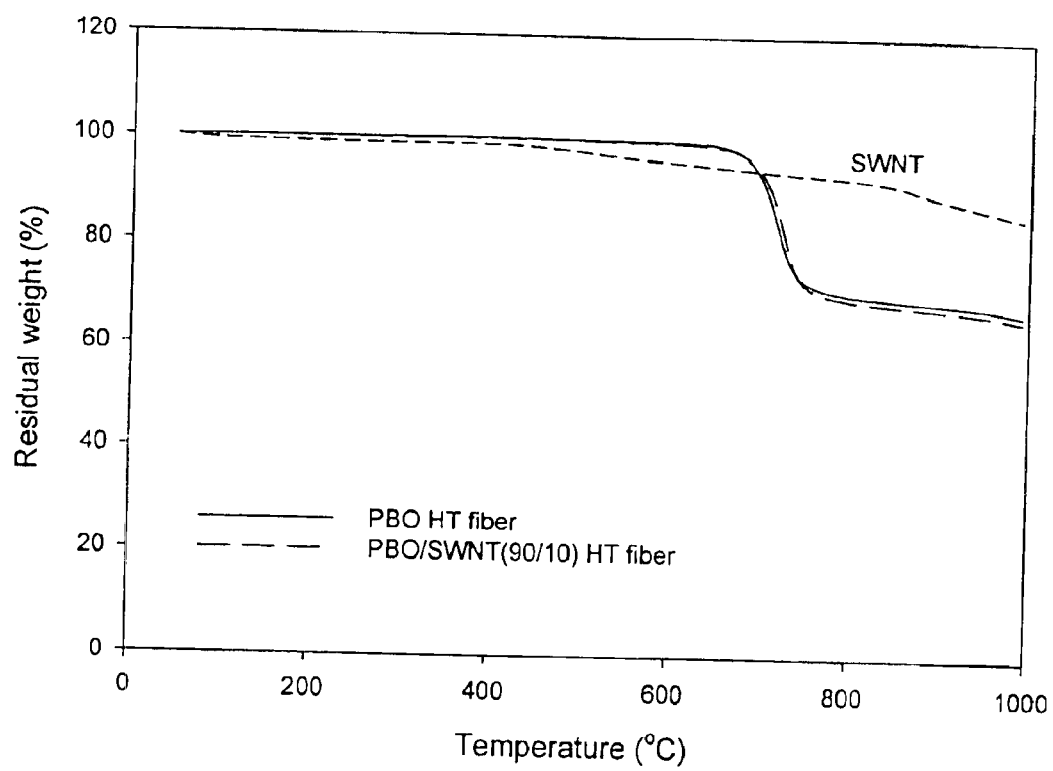
FIG. 4 shows weight loss in PBO, PBO/SWNT (90/10), and SWNT when heated at 20° C./minute in nitrogen.

The coefficient of thermal expansion (CTE) was measured for PBO and PBO/SWNT (90/10) fibers. The CTE data for the PBO and PBO/SWNT (90/10) fibers, shown in FIG. 2, are −6 and −4 parts per million (ppm) per ° C., respectively. PBO/SWNT (90/10) also exhibits reduced high temperature creep (measured using a TA Instruments TMA 2940) as compared to the control PBO fiber, as, as shown in FIG. 3. Thermal degradation for PBO/SWNT and PBO, conducted at 10° C./min using a TA Instruments TGA 2950, were comparable, as shown in FIG. 4.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A composition comprising a rigid-rod polymer and carbon nanotubes, wherein the rigid-rod polymer is a polymer comprising a repeat group of the formula

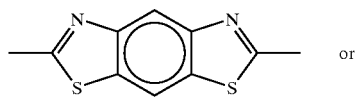 or

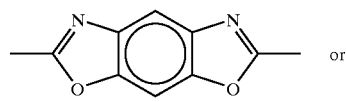.

2. A composition comprising a rigid-rod polymer and carbon nanotubes, wherein the rigid-rod polymer is a polymer comprising a repeat group of the formula

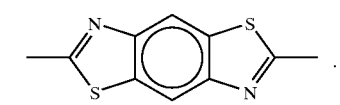 or

.

3. A composition comprising a rigid-rod polymer and carbon nanotubes, wherein the rigid-rod polymer is a polymer comprising a repeat group of the formula

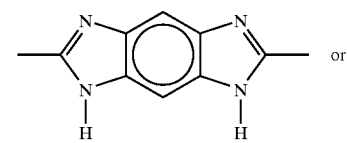

4. A composition comprising a rigid-rod polymer and carbon nanotubes, wherein the rigid-rod polymer is a polymer comprising a repeat group of the formula

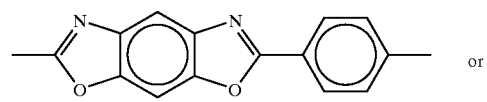 or

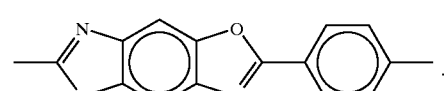.

5. A composition comprising a rigid-rod polymer and carbon nanotubes, wherein the rigid-rod polymer is a polymer comprising a repeat group of the formula

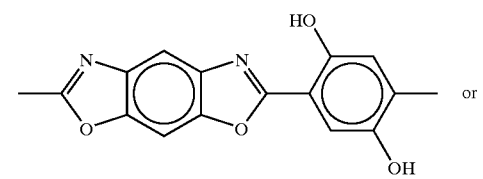 or

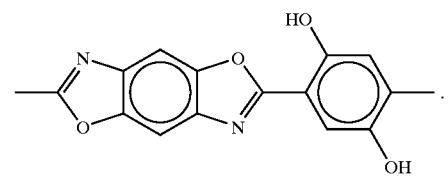.

6. A composition comprising a rigid-rod polymer and carbon nanotubes, wherein the rigid-rod polymer is a polymer comprising a repeat group of the formula

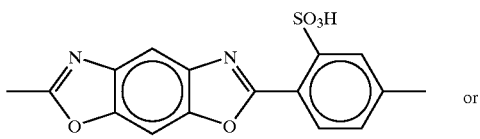

or

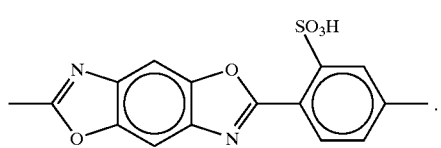

.

7. A composition comprising a rigid-rod polymer and carbon nanotubes, wherein the rigid-rod polymer is a polymer comprising a repeat group of the formula

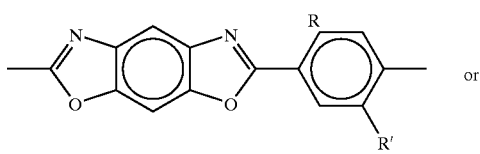

or

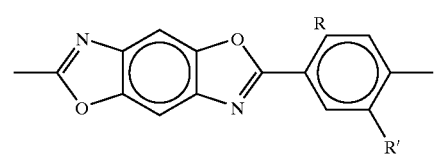

wherein R is —CH₃ and R' is —CH₃ or R is —CH₃ and R' is —H.

8. A composition comprising a rigid-rod polymer and carbon nanotubes, wherein the rigid-rod polymer is a polymer comprising a repeat group of the formula

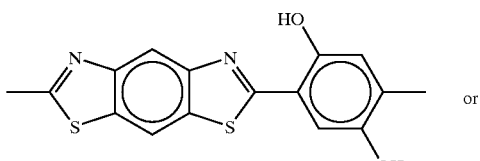

or

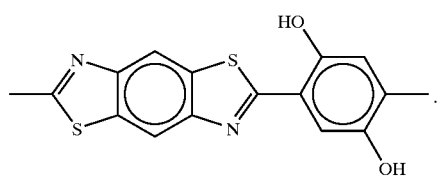

.

9. A composition comprising a rigid-rod polymer and carbon nanotubes, wherein the rigid-rod polymer is a polymer comprising a repeat group of the formula

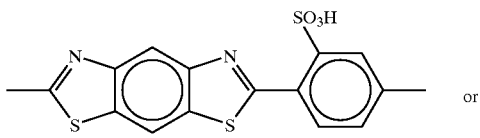

or

-continued

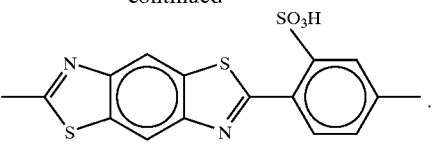

.

10. A composition comprising a rigid-rod polymer and carbon nanotubes, wherein the rigid-rod polymer is a polymer comprising a repeat group of the formula

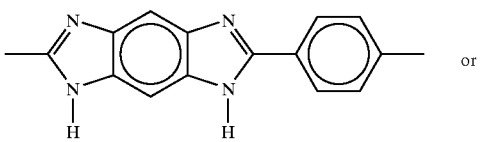

or

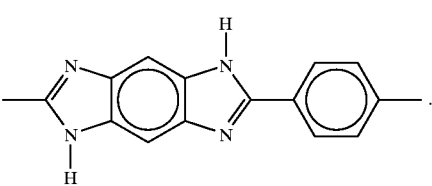

.

11. A composition comprising a rigid-rod polymer and carbon nanotubes, wherein the rigid-rod polymer is a polymer comprising a repeat group of the formula

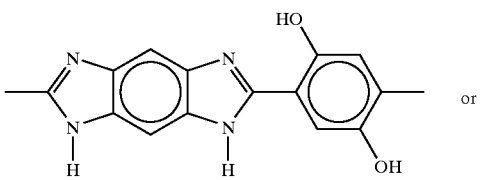

or

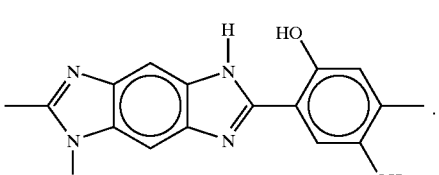

.

12. A composition comprising a rigid-rod polymer and carbon nanotubes, wherein the rigid-rod polymer is a polymer comprising a repeat group of the formula

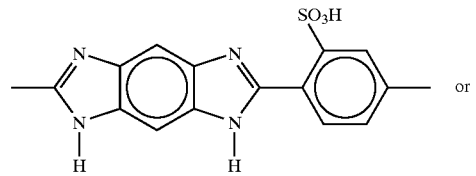

or

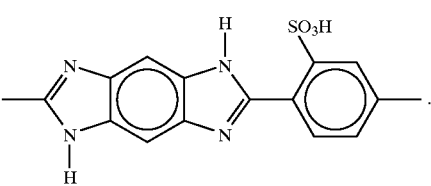

.

13. A composition comprising a rigid-rod polymer and carbon nanotubes, wherein the rigid-rod polymer is a polymer comprising a repeat group of the formula

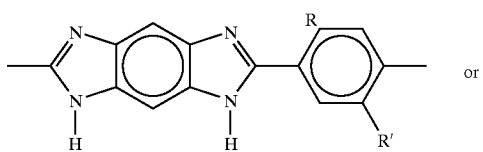 or

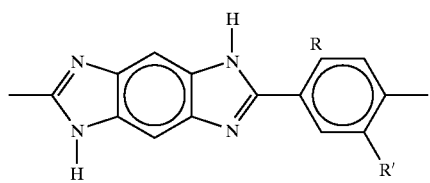

wherein R is —CH₃ and R' is —CH₃ or R is —CH₃ and R' is —H.

14. A composition comprising a rigid-rod polymer and carbon nanotubes, wherein the rigid-rod polymer is a polymer comprising a repeat group of the formula

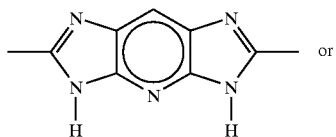 or

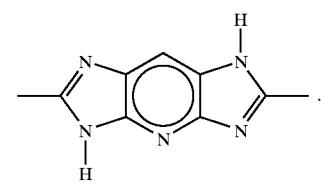

15. A composition comprising a rigid-rod polymer and carbon nanotubes, wherein the rigid-rod polymer is a polymer comprising a repeat group of the formula

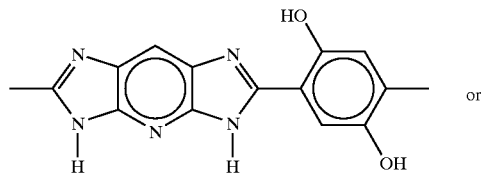 or

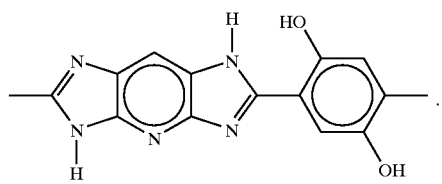

16. A composition comprising a rigid-rod polymer and carbon nanotubes, wherein the rigid-rod polymer is a polymer comprising a repeat group of the formula

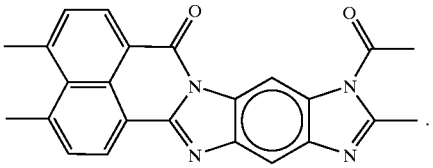

17. A fiber comprising a rigid-rod polymer and carbon nanotubes, wherein the rigid-rod polymer is a polymer comprising a repeat group of the formula

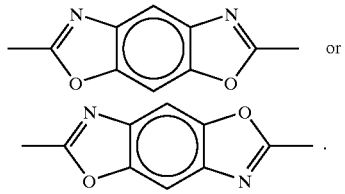

18. A fiber comprising a rigid-rod polymer and carbon nanotubes, wherein the rigid-rod polymer is a polymer comprising a repeat group of the formula

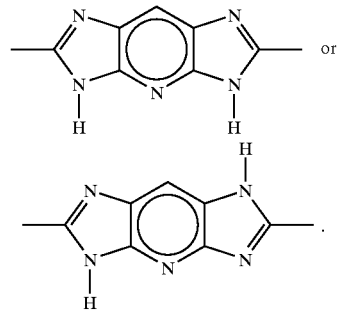

19. A fiber comprisinn a rigid-rod polymer and carbon nanotube,s wherein the rigid-rod polymer is a polymer comprising a repeat group of the formula

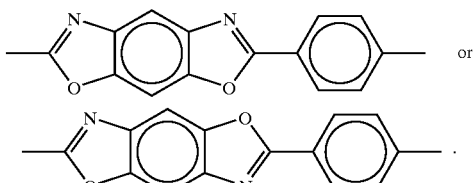 or

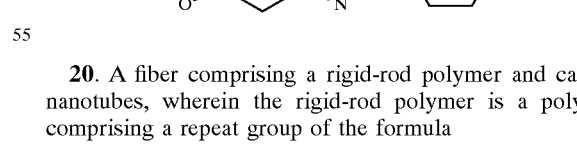

20. A fiber comprising a rigid-rod polymer and carbon nanotubes, wherein the rigid-rod polymer is a polymer comprising a repeat group of the formula

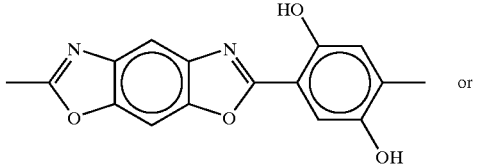 or

-continued

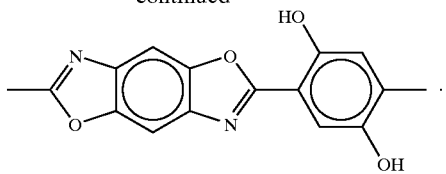

21. A fiber comprising a rigid-rod polymer and carbon nanotubes, wherein the rigid-rod polymer is a polymer comprising a repeat group of the formula

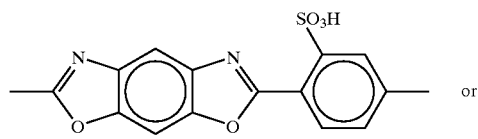

or

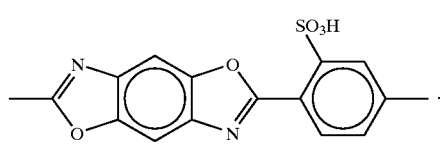

.

22. A fiber comprising a rigid-rod polymer and carbon nanotubes, wherein the rigid-rod polymer is a polymer comprising a repeat group of the formula

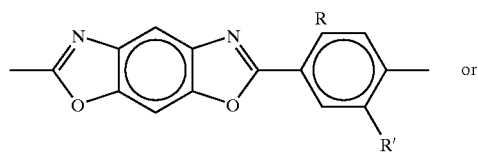

or

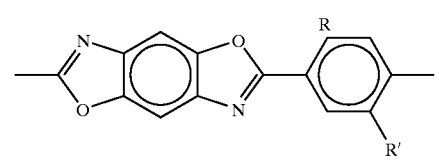

wherein R is —CH$_3$ and R' is —CH$_3$ or R is —CH$_3$ and R' is —H.

23. A fiber comprising a rigid-rod polymer and carbon nanotubes, wherein the rigid-rod polymer is a polymer comprising a repeat group of the formula

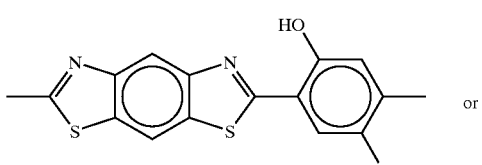

or

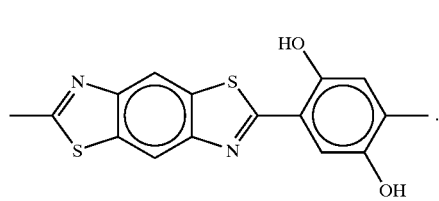

.

24. A fiber comprising a rigid-rod polymer and carbon nanotubes, wherein the rigid-rod polymer is a polymer comprising a repeat group of the formula

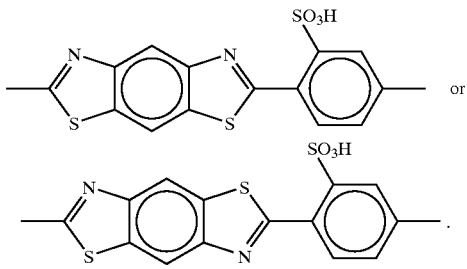

or

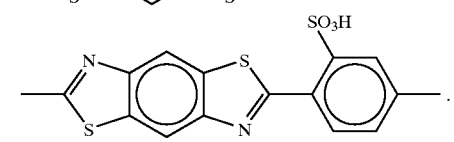

.

25. A fiber comprising a rigid-rod polymer and carbon nanotubes, wherein the rigid-rod polymer is a polymer comprising a repeat group of the formula

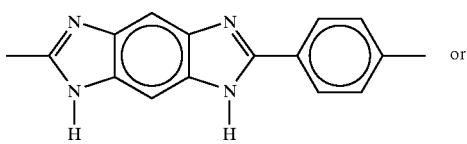

or

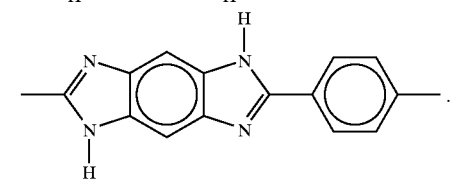

.

26. A fiber comprising a rigid-rod polymer and carbon nanotubes, wherein the rigid-rod polymer is a polymer comprising a repeat group of the formula

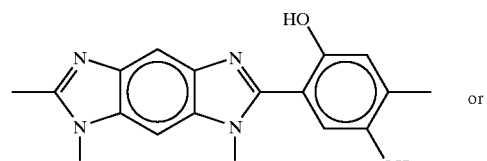

or

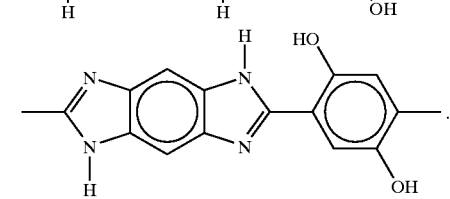

.

27. A fiber comprising a rigid-rod polymer and carbon nanotubes, wherein the rigid-rod polymer is a polymer comprising a repeat group of the formula

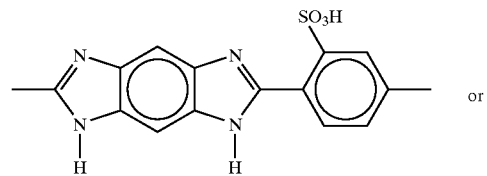

or

23

-continued

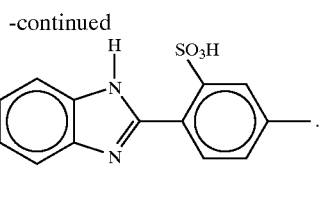

28. A fiber comprising a rigid-rod polymer and carbon nanotubes, wherein the rigid-rod polymer is a polymer comprising a repeat group of the formula

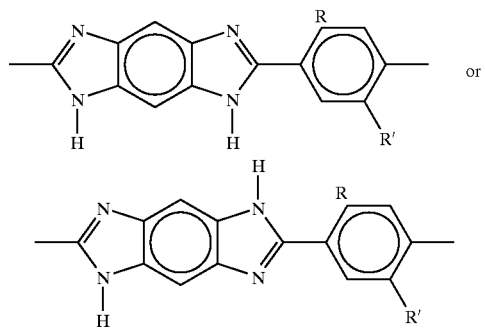

wherein R is —CH$_3$ and R' is —CH$_3$ or R is —CH$_3$ and R' is —H.

29. A fiber comprising a rigid-rod polymer and carbon nanotubes, wherein the rigid-rod polymer is a polymer comprising a repeat group of the formula

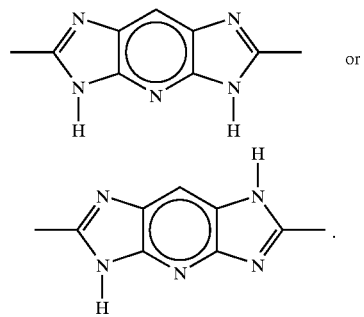

30. A fiber comprising a rigid-rod polymer and carbon nanotubes, wherein the rigid-rod polymer is a polymer comprising a repeat group of the formula

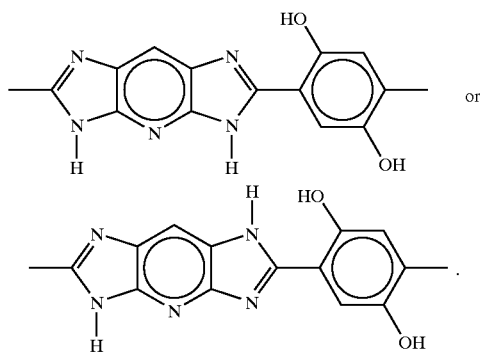

24

31. A fiber comprising a rigid-rod polymer and carbon nanotubes, wherein the rigid-rod polymer is a polymer comprises a repeat group of the formula

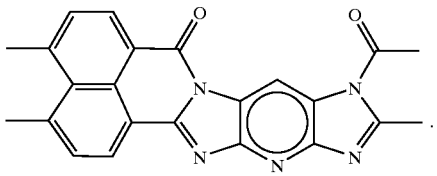

32. A film comprising a rigid-rod polymer and carbon nanotubes, wherein the rigid-rod polymer comprises a benzobisazole polymer comprising a repeat group of the formula

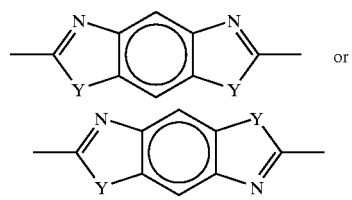

wherein Y is —O—, —S— or —NR', wherein R' is selected from the group consisting of —H, alkyl having 1 to 4 carbon atoms, and an aromatic group having 1 or 2 aromatic rings.

33. A film comprising a rigid-rod polymer and carbon nanotubes, wherein the rigid-rod polymer comprises a para-ordered heterocyclic polymer comprising a repeat group of the formula

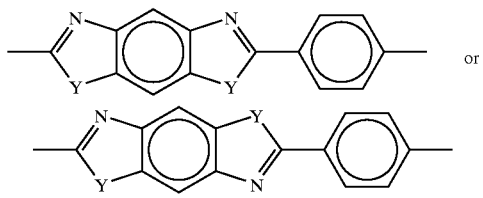

wherein Y is —S—, —O—, or —NR', and wherein R' is —H, an alkyl group having 1 to 4 carbon atoms or an aromatic group having 1 or 2 aromatic rings.

34. A film comprising a rigid-rod polymer and carbon nanotubes, wherein the rigid-rod polymer comprises a para-ordered heterocyclic polymer comprising a repeat group of the formula

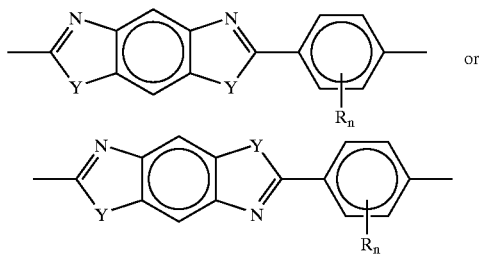

wherein Y is —S—, —O—, —NR', n is 1 or 2, R is a hydroxyl group, a sulfo group or an alkyl group having 1 to 4 carbon atoms and R' is —H, an alkyl group having 1 to 4 carbon atoms or an aromatic group having 1 or 2 aromatic rings.

35. The film of claim 34 wherein n is 1.

36. The film of claim 35 wherein R is —HSO₃.

37. The film of claim 35 wherein R is —CH₃.

38. The film of claim 34 wherein n is 2.

39. The film of claim 38 wherein R is —CH₃.

40. The film of claim 38 wherein R is —OH.

41. A film comprising a rigid-rod polymer and carbon nanotubes, wherein the rigid-rod polymer is a polymer comprising a repeat group of the formula

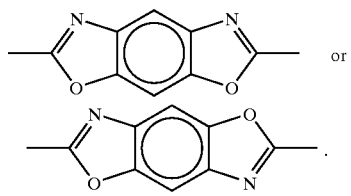

or

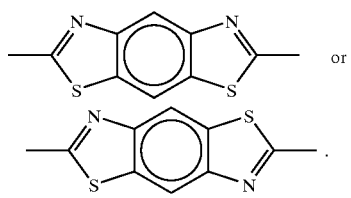

.

42. A film comprising a rigid-rod polymer and carbon nanotubes, wherein the rigid-rod polymer is a polymer comprising a repeat group of the formula

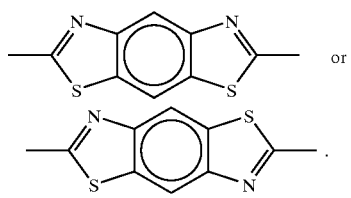

or

.

43. A film comprising a rigid-rod polymer and carbon nanotubes, wherein the rigid-rod polymer is a polymer comprising a repeat group of the formula

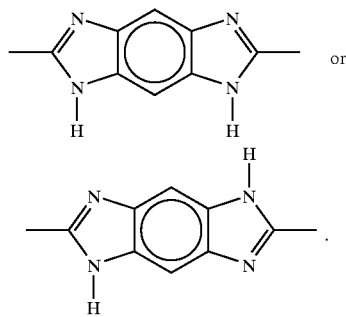

or

.

44. A film comprising a rigid-rod polymer and carbon nanotubes, wherein the rigid-rod polymer is a polymer comprising a repeat group of the formula

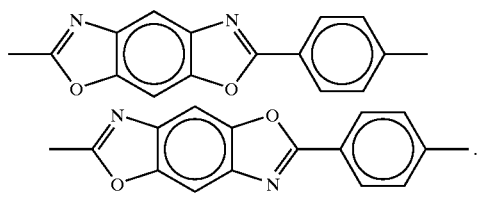

or

.

45. A film comprising a rigid-rod polymer and carbon nanotubes, wherein the rigid-rod polymer is a polymer comprising a repeat group of the formula

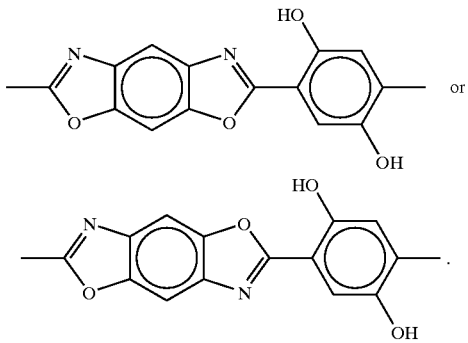

or

.

46. A film comprising a rigid-rod polymer and carbon nanotubes, wherein the rigid-rod polymer is a polymer comprising a repeat group of the formula

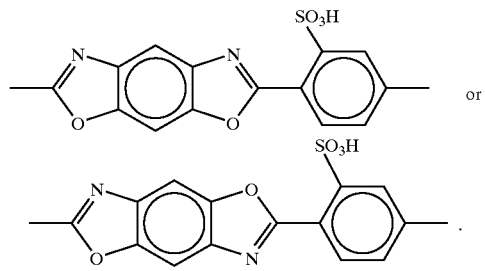

or

.

47. A film comprising a rigid-rod polymer and carbon nanotubes, wherein the rigid-rod polymer is a polymer comprising a repeat group of the formula

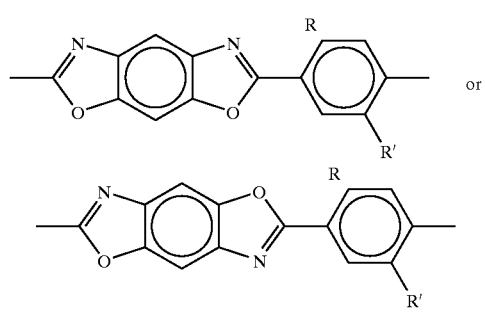

or

.

wherein R is —CH₃ and R' is —CH₃ or R is —CH₃ and R' is —H.

48. A film comprising a rigid-rod polymer and carbon nanotubes, wherein the rigid-rod polymer is a polymer comprising a repeat group of the formula

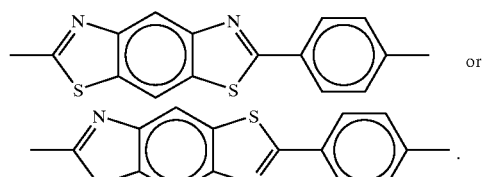

or

.

49. A film comprising a rigid-rod polymer and carbon nanotubes, wherein the rigid-rod polymer is a polymer comprising a repeat group of the formula

[structure: benzobisthiazole linked to phenyl with HO and OH substituents] or

[structure: benzobisthiazole (cis isomer) linked to phenyl with HO and OH substituents].

50. A film comprising a rigid-rod polymer and carbon nanotubes, wherein the rigid-rod polymer is a polymer comprising a repeat group of the formula

[structure: benzobisthiazole linked to phenyl with SO$_3$H substituents] or

[structure: benzobisthiazole (cis) linked to phenyl with SO$_3$H substituent].

51. A film comprising a rigid-rod polymer and carbon nanotubes, wherein the rigid-rod polymer is a polymer comprising a repeat group of the formula

[structure: benzobisthiazole linked to phenyl with R and R' substituents] or

[structure: benzobisthiazole (cis) linked to phenyl with R and R' substituents].

wherein R is —CH$_3$ and R' is —CH$_3$ or R is —CH$_3$ and R' is —H.

52. A film comprising a rigid-rod polymer and carbon nanotubes, wherein the rigid-rod polymer is a polymer comprising a repeat group of the formula

[structure: benzobisimidazole linked to phenyl] or

[structure: benzobisimidazole (alternate) linked to phenyl].

53. A film comprising a rigid-rod polymer and carbon nanotubes, wherein the rigid-rod polymer is a polymer comprising a repeat group of the formula

[structure: benzobisimidazole linked to phenyl with HO and OH substituents] or

[structure: benzobisimidazole (alternate) linked to phenyl with HO and OH substituents].

54. A film comprising a rigid-rod polymer and carbon nanotubes, wherein the rigid-rod polymer is a polymer comprising a repeat group of the formula

[structure: benzobisimidazole linked to phenyl with SO$_3$H substituent] or

[structure: benzobisimidazole (alternate) linked to phenyl with SO$_3$H substituent].

55. A film comprising a rigid-rod polymer and carbon nanotubes, wherein the rigid-rod polymer is a polymer comprising a repeat group of the formula

[structure: benzobisimidazole linked to phenyl with R and R' substituents] or

[structure: benzobisimidazole (alternate) linked to phenyl with R and R' substituents].

wherein R is —CH$_3$ and R' is —CH$_3$ or R is —CH$_3$ and R' is —H.

56. A film comprising a rigid-rod polymer and carbon nanotubes, wherein the rigid-rod polymer is a polymer comprising a repeat group of the formula

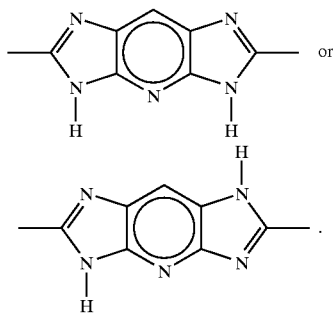

or

57. A film comprising a rigid-rod polymer and carbon nanotubes, wherein the rigid-rod polymer is a polymer comprising a repeat group of the formula

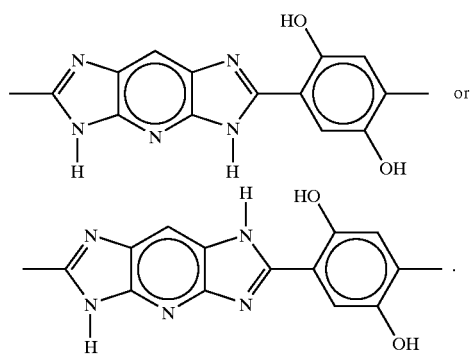

58. A film comprising a rigid-rod polymer and carbon nanotubes, wherein the rigid-rod polymer is a polymer comprising a repeat group of the formula

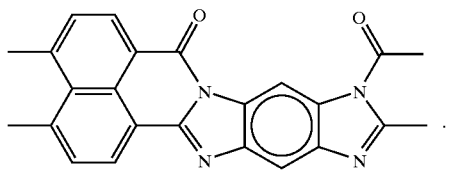

59. The method for preparing a composite comprising a rigid-rod polymer and a carbon nanotube, comprising polymerizing a rigid-rod polymer in the presence of carbon nanotubes.

60. The method of claim 59 wherein the polymer is a liquid crystalline polymer.

61. The method of claim 59 wherein the polymerizing is by polycondensation.

62. The method of claim 59 wherein the carbon nanotubes are selected from the group consisting of single-wall carbon nanotubes, multi-wall carbon nanotubes and a combination thereof.

63. The method of claim 59 wherein the rigid-rod polymer comprises a benzobisazole polymer comprising a repeat group of the formula

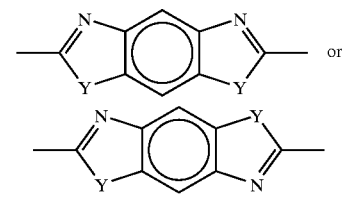

or wherein Y is —O—, —S— or —NR', wherein R' is selected from the group consisting of —H, alkyl having 1 to 4 carbon atoms, and an aromatic group having 1 or 2 aromatic rings.

64. The method of claim 59 wherein the rigid-rod polymer comprises a para-ordered heterocyclic polymer comprising a repeat group of the formula

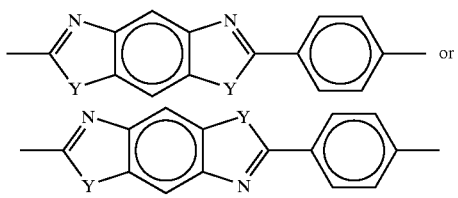

or wherein Y is —S—, —O—, or —NR', and wherein R' is —H, an alkyl group having 1 to 4 carbon atoms or an aromatic group having 1 or 2 aromatic rings.

65. The method of claim 59 wherein the rigid-rod polymer comprises a para-ordered heterocyclic polymer comprising a repeat groups of the formula

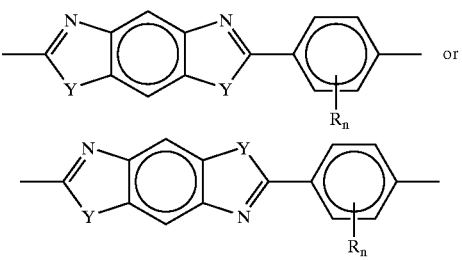

or wherein Y is —S—, —O—, —NR', n is 1 or 2, R is a hydroxyl group, a sulfo group or an alkyl group having 1 to 4 carbon atoms and R' is —H, an alkyl group having 1 to 4 carbon atoms or an aromatic group having 1 or 2 aromatic rings.

66. The method of claim 65 wherein n is 1.
67. The method of claim 66 wherein the R is —HSO$_3$.
68. The method of claim 66 wherein R is —CH$_3$.
69. The method of claim 65 wherein n is 2.
70. The method of claim 69 wherein R is —CH$_3$.
71. The method of claim 69 wherein R is —OH.
72. The method of claim 59 wherein the rigid-rod polymer is a polymer comprising a repeat group of the formula

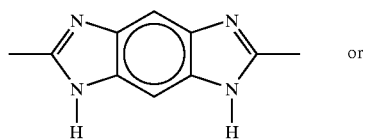

or

-continued

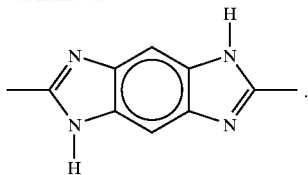

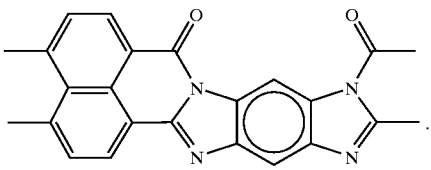

73. The method of claim 59 wherein the rigid-rod polymer is a polymer comprising a repeat group of the formula

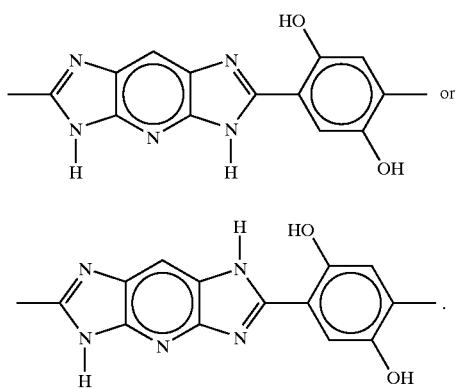

or

74. The method of claim 59 wherein the rigid-rod polymer is a polymer comprising a repeat group of the formula 75. The method of claim 59 further comprising spinning the composite into a fiber.

76. The method of claim 75 wherein the fiber is spun by the dry-jet wet technique.

77. The method of claim 75 further comprising washing and drying the fiber.

78. The method of claim 75 further comprising heat treating the fiber.

79. An article comprising the fiber of claim 17.

80. The article of claim 79 wherein the article is selected from the group consisting of vehicle armor, bullet-proof vests, body armor and armor for a structure.

81. The article of claim 79 wherein the article is an element of a ballistic protection system.

82. An article comprising a film, wherein the film comprises a rigid-rod polymer and carbon nanotubes, wherein the article is selected from the group consisting of vehicle armor, bullet-proof vests, body armor and armor for a structure.

83. An article comprising a film, wherein the film comprises a rigid-rod polymer and carbon nanotubes, wherein the article is an element of a ballistic protection system.

* * * * *

UNITED STATES PATENT AND TRADEMARK OFFICE
CERTIFICATE OF CORRECTION

PATENT NO. : 6,900,264 B2 Page 1 of 1
DATED : May 31, 2005
INVENTOR(S) : Satish Kumar, Fred E. Arnold and Thuy D. Dang It is certified that error appears in the above-identified patent and that said Letters Patent is hereby corrected as shown below:

Column 20,
Line 43, delete "comprisinn" and insert -- comprising --.
Line 44, delete "nanotube,s" and insert -- nanotubes --.

Signed and Sealed this

Sixteenth Day of August, 2005

JON W. DUDAS
*Director of the United States Patent and Trademark Office*